US005446143A

United States Patent [19]
Simpson et al.

[11] Patent Number: 5,446,143
[45] Date of Patent: Aug. 29, 1995

[54] ADIPOSE-SPECIFIC PROMOTER REGION OF HUMAN AROMATASE CYTOCHROME P450 GENE

[75] Inventors: Evan R. Simpson, Dallas; Mala S. Mahendroo; Carole R. Mendelson, both of Arlington, all of Tex.

[73] Assignee: Board of Regents, the University of Texas System, Austin, Tex.

[21] Appl. No.: 121,063

[22] Filed: Sep. 14, 1993

[51] Int. Cl.$^6$ .................... C12N 15/11; C12N 15/09
[52] U.S. Cl. ......................... 536/24.1; 435/69.1; 435/172.3
[58] Field of Search .............. 536/24.1; 435/172.3, 435/69.1

[56] References Cited

PUBLICATIONS

Harada et al., "Structural Characterization of the Human Estrogen Synthetase (Aromatase) Gene," *Biochemical and Biophysical Research Communications*, 166(1):365-372, 1990.

Kilgore et al., "Alternative Promotion of Aromatase P-450 Expression in the Human Placenta," *Molecular and Cellular Endocrinology*, 83:R9-R16, 1992.

Mahendroo et al., "Tissue—specific Expression of Human P-450," *The Journal of Biological Chemistry*, 266(17):11276-11281, 1991.

Mahendroo et al., "Tissue—Specific and Hormonally—Controlled Alternative Promoters Regulate Aromatase Cytochrome P450 Gene Expression in Human Adipose Tissue," *Journal of Biological Chemistry*, 268(26):19463-19470, 1993.

Means et al., "Tissue—Specific Promoters Regulate Aromatase Cytochrome P450 Gene Expression in Human Ovary and Fetal Tissues," *Molecular Endocrinology*, 5(12):2005-2013, 1991.

Means et al., "Structural Analysis of the Gene Encoding Human Aromatase Cytochrome P-450, the Enzyme Responsible for Estrogen Biosynthesis," *The Journal of Biological Chemistry*, 264(32):19385-19391, 1989.

Simpson et al., "Regulation of Human Aromatase Cytochrome P450 Gene Expression," *J. Steroid Biochem. Molec. Biol.*, 43(8):923-930, 1992.

Simpson et al., "Regulation of Expression of the Genes Encoding Steroidogenic Enzymes," *J. Steriod Biochem. Molec. Biol.*, 40(1-3), 1991.

Simpson et al., "Tissue—Specific Promoters Regulate Aromatase Cytochrome P450 Expression," *Clinical Chemistry*, 39(2):317-324, 1993.

Toda et al., "Characterization of a cis—acting regulatory element involved in human—aromatase P-450 gene expression," *Eur. J. Biochem.*, 205:303-309, 1992.

Toda et al., "Structural and functional characterization of human aromatase P-405 gene," *Eur. J. Biochem.*, 193:559-565, 1990.

Wang and Chen, "Identification of a Promoter and a Silencer at the 3'—End of the First Intron of the Human Aromatase Gene," *Molecular Endocrinology*, 6(9):1479-1488, 1992.

Zhou et al., "Stable Expression of Human Aromatase Complementary DNA in Mammalian Cells: A Useful System for Aromatase Inhibitor Screening," *Cancer Research*, 50:6949-6954, 1990.

*Primary Examiner*—Richard A. Schwartz
*Assistant Examiner*—Nancy T. Vogel
*Attorney, Agent, or Firm*—Arnold, White & Durkee

[57] ABSTRACT

The present invention relates generally to the control and regulation of estrogen biosynthesis. Estrogen biosynthesis is catalyzed by a microsomal enzyme, aromatase cytochrome P450 (P450arom; the product of the CYP19 gene). Tissue-specific expression of P450arom is determined by the use of tissue-specific promoters which give rise to P450arom transcripts with unique 5' noncoding sequences. Two unique 5'-untranslated exons of the CYP19 gene, I.3 and I.4., which are present in adipose tissue and adipose stromal cells (ASC) in culture have been identified. I.3-specific sequence is expressed in adipose tissue as well as in ACS maintained under all culture conditions, I.4-specific sequence is apparently present only in breast adipose tissue, and ACS stimulated with gluocorticoids.

1 Claim, 11 Drawing Sheets

Exon I.3 and Exon II

GGCTTTCAATTGGGAATGCAGTCACTCTACCCACTCAAGGGCAAGATGATAAGGTTCTATCAGACCAAGCGTC
TAAGGAACCTGAGACTCTACCAAGGTCAGAAATGCTGCAATTCAAGCCAAAAGATCTTTCTTGGGCTTCCTTG
TTTGACTTGTAACCATAAATTAGTCTTGCCTAAATGTCTGATCACATTATAAACAGACTCTAAATTGCCCCC
TCTGAGGTCAAGGAACACAAGATGGTTTTGGAAATGCTGAACCCGATACATTATAACATCACCAGCATCGTGCC
                        MetValLeuGluMetLeuAsnProIleHisTyrAsnIleThrSerIleValPr
TGAAGGCCATGCCTGCTGCCACCATGCCTGAAGCCATGCTGCCGAAGCCATGCCGAAGCCATGCTCTGCTGCCAGTCCT
oGluAlaMetProAlaAlaThrMetProValL
GCACATCCTCAATACCAG
lyThrSerIlePro

I.3-truncate and Exon II

GGCTTTCAATTGGGAATGCAGTCACTCTACCCACTCAAGGGCAAGATGATAAGGTTCTATCAGACCAAGCGTC
TAAAGGAACCTGAGACTCTACCAAGGACTCTAAATTGCCCCCTCTGAGGTCAAGGAACACAAGATGGTTTTGGA
                                                                MetValLeuGl
AATGCTGAACCCGATACATTATAACATCACCAGCATCGTGCCGAAGCCATGCCTGCTGCCACCATGCCAGTCCT
uMetLeuAsnProIleHisTyrAsnIleThrSerIleValProGluAlaMetProAlaAlaThrMetProValL
GCTCCTCACTGGCCTTTTCTCTTGGTGTGGAATTATGAGGGCACATCCTCAATACCAG
euLeuLeuThrGlyLeuPheLeuLeuValTrpAsnTyrGluGlyThrSerIlePro

FIG. 1A

Exon I.4 and Exon II

AACCATGACAGCCACAGTCAGGACACAAAAAACAAAGTGTCCTTGATCCCAGGAAACAGCCCTCTGGAATCTGTG
AAATCTAGAAACATAGTTGGGAAAACTCTGACACCCTGCCCCTGCCCCTCCAGGAGATCCCTGACCATGTGGGGCATG
TGAGGTCACAGAAGGCAGAGAGCCTGCTCCCTCCAAGTAGAACGTGACCAACTGGAGAGCCTGACAGGAGGTCCCTGGC
AGTGATGTGATGGGAAACTGGCTCCCTGGCTCCAAGTAGAACGTGACCAACTGGAGAGCCTGACAGGAGGTCCCTGGC
ACTGGTCAGGCCATCAAACCAGGACTCTAAATTGCCCCTCTGAGGTCAAGGAACACAAGATGGTTTTGGAAATG
                                                     MetValLeuGluMet
CTGAACCCGATACATTATAACATCACCAGCATCGTGCCTGAAGCCATGCCTGCCTGAAGCCATGCCTGCCACCAGTCCTGCTC
LeuAsnProIleHisTyrAsnIleThrSerIleValProGluAlaMetProAlaAlaThrMetProValLeuLeu
CTCACTGGCCTTTTCTCTCTTGGTGTGTGGAATTATGAGGGCACATCCTCAATACCAG
LeuThrGlyLeuPheLeuLeuValTrpAsnTyrGluGlyThrSerSerIleProG

FIG. 1B

Exon I.4, exon I.2 and Exon II

AAGTAGAACGTGACCAACTGGAGGCCTGACAGGAGGTCCCTGGCACTGGTCAGCAGCCCATCAAACCAGGACCGCTGA
TAACAGCTTCATGTGGAACTTGGGAACTTGGGATTAATATCAAGCAAGCCATGGATTTGTCTCCACTGAACTTGGGCATC
ATGGACAGTTTCCATTCCAGCAGTTAAGGGCTTCCTGACTTTCAACAGTGGTGCTGATCCCAGTTCGAAGAGT
GGAACATCAGAGAGCCTCCCTCAGCCACTTGACTCTAAATTGCCCCTCTGAGGTCAAGGAACACAAGAT
                                                                   Me

GGTTTTGGAAATGCTGAACCCGATACATTATAACATCCAGCATCGTGCCTGAAGCCATGCCTGCTGCCACCA
tValLeuGluMetLeuAsnProIleHisTyrAsnIleThrSerIleValProGluAlaMetProAlaAlaThrM
TGCCAGTCCTGCTCCTCACTGGCCTTTTCTCTTGGTGTGGAATTATGAGGGCACATCCTCAATACCAG
etProValLeuLeuLeuThrGlyLeuPheLeuLeuValTrpAsnTyrGluGlyThrSerSerIleProG

Promoter II-specific Sequence

GCACCCTCTGAAGCAACAGGAGCTATAGATGAACCTTTTAGGGGATTCTGTAATTTTCTGTCCCTTGATTTC
CACAGGACTCTAAATTGCCCCTCTGAGGTCAAGGAACAAGATGGTTTTGGAAATGCTGAACCGATACATT
                                         MetValLeuGluMetLeuAsnProIleHisT

ATAACATCACCAGCATCGTGCCTGAAGCCATGCCTGCTGCCACCATGCCTGTCCTGCTCCTCACTGGCCTTTT
yrAsnIleThrSerIleValProGluAlaMetProAlaAlaThrMetProValLeuLeuLeuThrGlyLeuPhe
CTCTTGGTGTGGAATTATGAGGGCACATCCTCAATACCAG
LeuLeuValTrpAsnTyrGluGlyThrSerSerIleProG

FIG. 1C

Exon IX 
-3.4 kb
-2.9 kb
Exon I.4 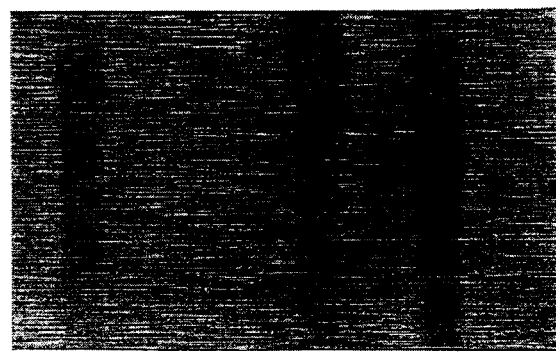
Exon I.3 
1　　　　2　　3
FIG. 4

1 2 3 4 5 6 7 8 ctctggtcagatattttgatcatgctacagtgcatgaaa
ttgttcataagaattgtatgtgcctctgtatctaacagg
atctgcttatatcttcagaaactttgtcataaatttaa
attacttaaagtgtctgatcttcagatactttaaagtag
tgcatttgagaatgggaatgttgattacagtgcgtatag
ggaaatagatgaatattccattaataactattaaaatct
gctaaagcttaggctaagctgatatatttagttgtaata
aaattgggtgaacacattccaacttcagcctgattaagg
gaaagggtgtaggggtgagacacttaggcggagcttaa
aaggaatggtgagagtttggccaatggaaggaaggctgt
gccagacaggaatagtgtgggctgacgacaactgagggc
aaagtgcttgtccctcatagttgcgcaatgaatgcaga
ggggctgaggttcatctgtcgtcttcagctctgcaggct
acatctcagggtgtttcctgtgaaagttccagaagaaag
ctgtatggtcagcttggggaaatatgtggttcatgctgg
aatgctggacataccacattggaaagatgcacattg
aatgaccgacaaatgaaactcaactttccaaatgctgg
taatgagagaagattctgttctaatgaccagttgtttcc
tgaaagaatgtcagctcgattcataatgaatgcattctA

FIG. 8A

ACCATGACAGCCACAGTCAGGACACAAAAAACAAAGTGT
CCTTGATCCCAGGAAACAGCCCTCTGGAATCTGTGAAAT
CTAGAAACATAGTTGGGAAAACTCTGACACCCCTGCCCC
ATGACCAACCAAGACTAAGAGTCCCAGAAGATTGAGGTC
ACAGAAGGCAGAGGCCTGCCCCCTCTCCAGGAGATCCCT
GACCCATGTGGGGTCATGGGCGGGGCATGAGTGATGTGA
TGGGAAACTGGCTCCTGGCTCCAAGTAGAACGTGACCAA
CTGGAGCCTGACAGGAGGTCCCTGGCACTGGTCAGCCCA
TCAAACCAGgtaagtccttggagtctgagtagggacaag
agactgttctgtgctttggcagggatcaggaagatgtta
gaatgtggttgttggaacttatctttggagctgaa

FIG. 8B

ADIPOSE-SPECIFIC PROMOTER REGION OF HUMAN AROMATASE CYTOCHROME P450 GENE

INTRODUCTION

The biochemical and physiological actions of estrogens include dimorphic anatomical, functional, and behavorial development of males and females that is essential for reproduction. Because of the importance of estrogen biosynthesis, understanding its regulation is essential to gain insights into the physiological and pathophysiological actions of estrogens. The biosynthesis of estrogens from androgens is catalyzed by an enzyme complex of the endoplasmic reticulum termed aromatase. The aromatase enzyme complex is composed of two polypeptides, NADPH-cytochrome P450 reductase, a ubiquitous flavoprotein of the endoplasmic reticulum, and aromatase cytochrome P450 (P450arom; the product of the CYP19 gene), a unique form of cytochrome P450, which appears to be present exclusively in estrogen-producing cells (1-5). The reaction involves three hydroxylation steps and requires NADPH-cytochrome P450 reductase to transfer reducing equivalents to the P450arom which binds the $C_{19}$ substrate and catalyzes insertion of oxygen into the molecule, resulting in formation of the $C_{18}$ estrogen (6-10).

In most species throughout the vertebrate phylum, estrogen biosynthesis is limited to the gonads and brain. In the human and other primates however, estrogen production has a wider tissue distribution which includes adipose tissue (11) and placenta (12). Studies showing an increased fractional conversion of circulating plasma and rostenedione to estrone as a function of increased obesity as well as increased age implicate adipose tissue as a significant site of estrogen biosynthesis (13,14) and as the major source of estrogens in postmenopausal woman and in elderly men. Unlike the ovary, estrogen production in adipose is not cyclic but continuous. While the physiological role of extragonadal estrogen production is not clear, there appears to be a relationship between estrogen biosynthesis in adipose and several disease states such as endometrial cancer, breast cancer and osteoporosis, as well as chronic amenorrhea of obese women and gynecomastia in obese men. Clearly, understanding the regulation of estrogen biosynthesis in adipose tissue will provide insights into the role of estrogens in these conditions.

Both cell types found in adipose tissue, namely adipocytes and adipose stromal cells, express aromatase, although much higher aromatase activity and expression of CYP19 transcripts have been observed in stromal cells (15,16). Adipose stromal cells in monolayer culture have been utilized as a model system to examine factors that regulate aromatase in vitro and to study CYP19 gene expression. A variety of factors have been shown to positively affect aromatase activity and P450arom expression in adipose stromal cells including glucocorticoids as well as cAMP analogs and phorbol esters. The stimulatory effects of dexamethasone require the presence of fetal calf serum (FCS) (17) in the medium while the increases induced by dibutyryl cAMP (Bt2cAMP) or Bt2cAMP+phorbol diacetate (PDA) are manifest only in the absence of FCS (18). A variety of growth factors including EGF, FGF, PDGF, TGFα, TGFβ, and TNF have been shown to mimic the inhibitory actions of FCS on Bt2cAMP- or Bt2cAMP+PDA-dependent increases in CYP19 expression (18,19).

Aromatase regulation by these agents is tissue-specific since in the ovary, glucocorticoids have little or no effect to stimulate aromatase activity and phorbol esters inhibit rather than potentiate the Bt2cAMP-induced stimulation of aromatase activity (20).

Isolation and characterization of the human CYP19 gene as well as the characterization of tissue-specific alternative promoters has led to the identification of one mechanism to explain the complex and tissue-specific regulation of P450arom expression. The human CYP19 gene spans at least 75 kb and is comprised of nine coding exons, exons II-X (21-23). Additionally, two noncoding exons, exon I.1 and I.2, have been previously described (21). In placenta, the majority of CYP19 transcripts contain exon I.1 in the 5' untranslated region (21,24) while a minor population of transcripts contain exon I.2 (25). Genomic sequences identified upstream of exon I.1 have been shown to regulate CYP19 gene transcription in placental-derived choriocarcinoma cells (23,26). Tissue-specific regulation of CYP19 expression by alternative promoters was first demonstrated in adipose stromal cells in culture (27). CYP19 transcripts in adipose tissue or in adipose stromal cells in culture do not contain either exon I.1 or I.2 sequences; thus promoters upstream of these exons most probably do not serve to regulate P450arom expression in these cells. By primer extension and S1 nuclease analysis using probes spanning the first coding exon, adipose stromal cells maintained in the presence of Bt2cAMP+PDA were shown to contain transcripts of which some 50% utilized a start site of transcription 26 bp downstream of a TATA-like sequence within the putative promoter-like sequence termed promoter II (PII), which is proximal to the start of translation (27). Additionally, the S1 nuclease protection assay was suggestive that at least 50% of adipose CYP19 transcripts may have an alternative transcriptional start site upstream of an exon that is not contiguous with exon II. The results of PCR experiments suggested that this exon(s) could not be either exon I.1 or I.2, and raised the possibility of another untranslated exon in the CYP19 gene, the transcription product of which is spliced onto exon II during processing of adipose stromal cell transcripts (27). CYP19 transcripts in the ovary also do not contain the placenta-specific exons I.1 and I.2, but the majority of transcripts have a start site of transcription 26 bp downstream of the TATA-like sequence within the putative promoter PII (24). Thus alternative promoters regulate CYP19 transcription giving rise to P450arom mRNAs with tissue-specific 5' untranslated sequences. These untranslated exons are spliced onto a common 3'-splice site upstream of the translational start site, thus the coding sequence is the same in all tissues.

SUMMARY OF THE INVENTION

The observation that additional transcriptional start sites might be utilized in adipose stromal cells led us to evaluate CYP19 transcripts in these cells as well as in adipose tissue for the presence of novel 5' noncoding sequences. Through construction of cDNA libraries from adipose tissue and adipose stromal cells, exon-specific northern analysis, and screening of genomic libraries, this work has led to a number of interesting and novel developments including the identification of two unique 5'-untranslated exons of human CYP19, as well as the observation that alternative promoter usage in adipose stromal cells in culture is a function of the hormonal environment under which the cells are maintained. Four P450arom transcripts with unique 5'-termini were identified, leading to the characterization of two unique 5'-untranslated exons of the CYP19 gene, I.3 and I.4. Whereas I.3-specific sequence is expressed in adipose tissue as well as in ACS maintained under all culture conditions, I.4-specific sequence is apparently present only in breast adipose tissue, and ACS stimulated with glucocorticoids. On the other hand, PII-specific sequence is present only in cells stimulated with cAMP analogues, and is absent from cells stimulated with glucocorticoids. We conclude that CYP19 gene expression in human adipose tissue likely utilizes two novel promoters, and furthermore that alternative promoter usage in cultured ASC is a function of the hormonal environment in which the cells are maintained.

BRIEF DESCRIPTION OF THE DRAWINGS

FIG. 1: Sequence of Two of the P450arom cDNA's, FIG. 1B: Sequence of One of the P450arom cDNA's. FIG. 1C: Sequence of Two of the P450arom cDNA's Identified in Adipose Tissue and Cells by the RACE Procedure. The sequences indicated represent the longest cDNA clone identified containing each particular 5' sequence. The four new 5' sequences and PII-specific sequences are underlined. All four of the new 5' sequences are spliced to the 5'-end of exon II at the same splice junction (The DNA and amino acid sequences in the five panels are represented by seq id no:1 through seq id no:6, with the DNA sequences being numbers 1, and 3-6; and the amino sequence being number 2).

FIG. 4: Northern Analysis of Adipose Stromal Cell poly(A)+RNA. RNA was prepared from breast adipose tissue from different donors than those in FIG. 3. The northern blot was repeatedly probed using 65-75 bp probes specific to an exon in the coding region (exon IX), exon I.3, and exon I.4. The probes were amplified and labelled by asymmetric PCR. Lane 1—40 µg poly(A)+RNA from cultured adipose stromal cells—serum; lane 2—40 µg poly (A)+RNA from cultured adipose stromal cells+serum; lane 3—40 µg poly(A)+RNA from cultured adipose stromal cells in the presence of serum and 250 nM dexamethasone. Exposure times were 4 days in the case of exon IX and I.4 probes, and 7 days in the case of the I.3 probe.

FIG. 8A and FIG. 8B: Sequence of the Genomic Clone containing Exon I.4 and Upstream Flanking Sequences(seq id no:7). FIG. 8A and 8B, when taken together form the sequence. Exon I.4 sequence as determined by the longest cDNA clone containing this exon is indicated in capital letters.

EXAMPLE I

MATERIALS AND METHODS

Figure 2:
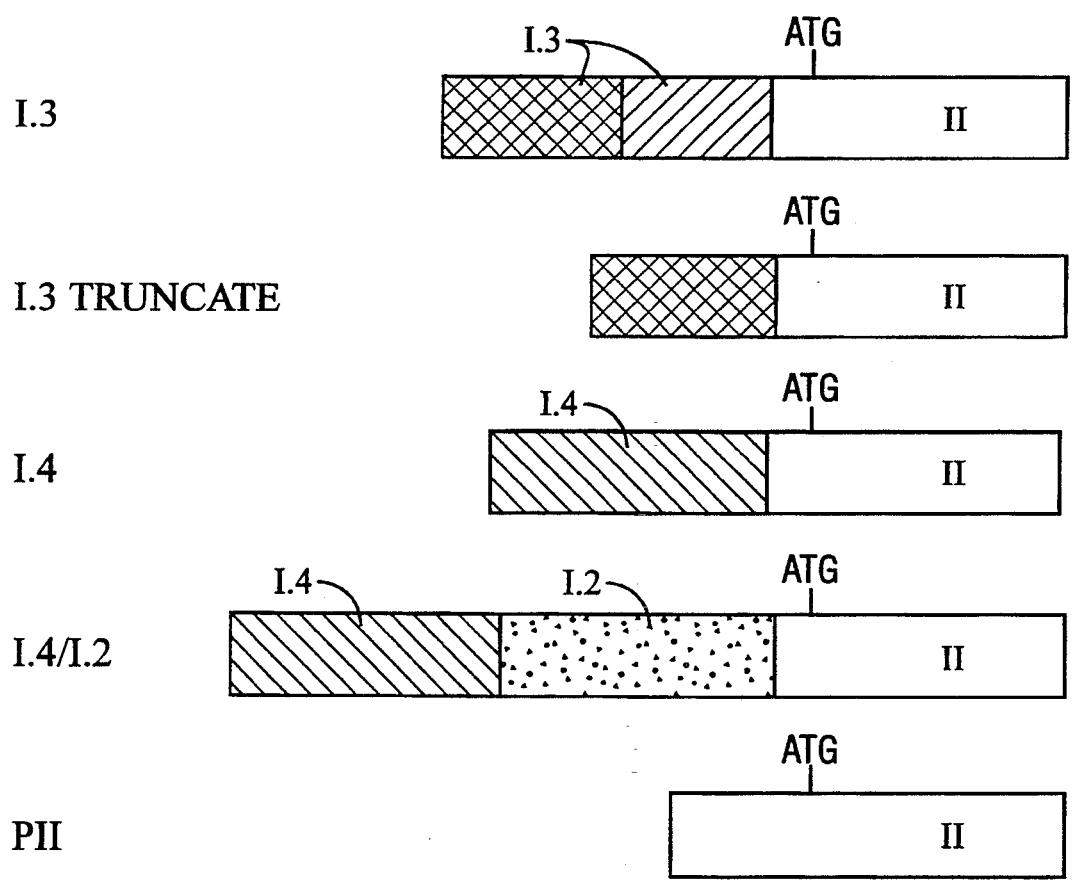
FIG. 2: Diagram of the Five cDNAs Isolated by the RACE Procedure. The diagram shows in schematic form the regions of identity between exons I.3 and I.3-truncate, and between exons I.4 and I.4/I.2.

Cell Cultures. Subcutaneous adipose tissue was obtained from women at the time of reduction abdominoplasty or reduction mammoplasty. Consent forms and protocols were approved by the Institutional Review Board, University of Texas Southwestern Medical Center at Dallas. Adipose stromal cells were maintained as primary cultures in Waymouths enriched medium containing Nu Serum (15%, v/v) (Collaborative Research Inc.). Adipose stromal cells were isolated as described (15). Upon reaching confluence the cells were placed in serum-free or FCS-containing (15%, v/v) Waymouths enriched medium for 24 hours. The cells were then treated with dibutyryl cAMP (0.5 mM), dibutyryl cAMP (0.5 mM)+phorbol diacetate (100 nM) in serum-free medium, or with dexamethasone (250 nM) in medium containing 15% FCS for 48 hours to maximally induce P450arom mRNA levels. Media were removed, and cells frozen at −70° C. until used for RNA isolation. Induction of aromatase activity was verified using the tritiated water release assay (15).

Isolation of RNA. Total RNA was isolated with minor modifications according to the method of Chirgwin et al. (29) from adipose tissue and adipose stromal cells in culture. Frozen whole tissue was crushed using a mortar and pestle and homogenized in guanidinium thiocyanate (G-SCN), pH 7.0 , using a Ultraturax T25 homogenizer. Dishes of frozen confluent adipose stromal cells were scraped in G-SCN. Poly (A)+RNA was isolated using oligo(dT) affinity chromatography (Type 2 oligo dT cellulose, Collaborative Research).

Rapid Amplification of cDNA Ends. cDNA libraries were constructed from adipose tissue, adipose stromal cells in control serum-free culture medium, medium containing $Bt_2cAMP+PDA$, or medium containing dexamethasone. Construction of RACE cDNAs was performed with minor modifications as described by Frohman et al. (30,31). The first step, first strand synthesis, was performed using 6 82 g of total RNA or 1 μg of poly (A+) RNA, 1 pmol primer 17 (located in exon III-5'ACTTYGCTGATAATGAGTGTT3'); (seq id no:8), reverse transcriptase buffer (Bethesda Research Laboratories-BRL), 1 mM DTT, 1 nM dNTPs, 200 units M-MLV reverse transcriptase (BRL), in a 20 μl volume. The primer extension was carried out at 44° C. for 1.5 h. Prior to the tailing step, the single-stranded cDNA was denatured at 65° C. for 5 min, placed on ice, and then tailed at the 3' end with poly(A) using the enzyme terminal transferase. The amplifications were performed using the Perkin Elmer Cetus buffer system, P450arom primer 24 (located in exon II-5'CTGGTATTGAGGATATGCCCTCATAAT3'); (seq id no:9), and Cetus Taq polymerase. An aliquot of the amplified product was run on a 1.8% agarose gel to visually estimate DNA concentrations. The cDNA was then ligated into the pCR2000 vector and transformed into INV1aF' competent cells using the TA Cloning System (Invitrogen Corporation). Positive colonies were screened using the tetramethyl ammonium chloride method as described (32). Positive clones were sequenced using the dsDNA Cycle Sequencing System (BRL).

RNA Blot-Hybridization Analysis. Both formaldehyde and glyoxal gel systems were utilized employing the method described by Maniatis et al. (33). Gels were routinely transferred to a charged membrane (Zeta Probe, Bio Rad) by capillary transfer as described by BioRad. The northerns were probed with PCR-amplified and -labelled 65–75 bp fragments specific to particular exons.

Screening and Sequence Analysis of an Human Genomic Library. A human genomic library constructed in an EMBL-3 Sp6/T7 lambda phage vector (Clontech Laboratories) was plated and screened with minor modifications by plaque hybridization using a PCR amplified and labelled 65 bp fragment specific to exon I.4 as a probe. Positive restriction fragments were identified by Southern analysis and subcloned into pUC$_{19}$ (BRL). Nucleotide sequence of the genomic clones was obtained by double-strand sequence analysis employing the dideoxy chain termination method using Sequenase (United States Biochemical Corp.).

Amplification of Specific Exons from RNA using Reverse Transcriptase-Polymerase Chain Reaction (RT-PCR). A single-stranded cDNA was synthesized using 8 μg of total RNA from breast adipose tissue together with 200 units MMLV-reverse transcriptase (Bethesda Research Laboratories) and 50 pmol of P450arom-specific oligonucleotides corresponding to regions of exon I.4, I.3, or II. The single-stranded cDNA was then amplified using exon I.4, I.4 and II, I.3, I.3 and II or II-specific primers. The amplified products were digested with RNase, separated on a 2% agarose gel, transferred to Zetaprobe (BioRad) and probed with a radiolabeled oligonucleotide complementary to sequence within the middle of exon II.

RESULTS

Characterization of cDNA libraries prepared from adipose tissue and adipose stromal cells. A putative promoter region, PII, 110 bp upstream of the first coding exon, namely exon II, was previously identified as a possible regulatory region for CYP19 transcripts in adipose stromal cells in culture treated with Bt2cAMP and PDA (27), and in corpus luteum tissue of the ovary (24). The identification of this putative promoter region was based solely on the identification of a transcriptional start site just downstream of a TATA-like sequence by S1 nuclease protection and primer extension analysis of adipose stromal cell and corpus luteum mRNA. To determine whether promoter II was capable of mediating transcriptional regulation in human adipose tissue, 935 bp of PII and upstream flanking sequence was ligated to a CAT reporter gene and transfected into human adipose stromal cells. Transfection of the −-935AROMCAT reporter construct into adipose stromal cells resulted in very low levels of CAT activity which were not appreciably induced by cAMP+PDA, while an RSVCAT construct containing the Rous sarcoma virus promoter linked to the CAT gene was capable of initiating transcription in these cells This observation suggested several possibilities: 1) sequences further upstream than −935 are required for promoter II activity; 2) sequences downstream of the first coding exon are required for promoter II activity; or 3) promoter II is not the major promoter regulating CYP19 expression in human adipose.

Based on the evidence of the previously published S1 nuclease protection analysis (27) suggesting different transcriptional start sites in addition to PII-specific CYP19 transcripts, as well as the initial transfection studies employing PII-specific reporter constructs, it appeared likely that adipose stromal cells in culture contain CYP19 transcripts with alternative 5' ends that are regulated by alternative promoters. In order to characterize the genomic regulatory regions upstream of these exons, it was important to identify unique sequences at the 5' ends of CYP19 transcripts in adipose tissue and in cultured stromal cells. Once these exons were identified, their sequences could be used as probes to determine their location relative to the rest of the CYP19 gene and thus to identify novel regulatory elements upstream of these untranslated exon(s).

Since the possibility existed that adipose tissue transcripts might contain more than one 5'-untranslated sequence, it was advantageous to construct the cDNA libraries so that many CYP19 cDNA clones could be readily isolated. Obtaining full-length cDNA clones of low abundance RNAs has proven to be difficult and laborious using traditional methods of cDNA cloning. However, utilizing a relatively new method of cDNA synthesis by PCR, a large number of cDNA clones can be identified rapidly. The method termed RACE (Rapid Amplification of cDNA Ends) (30,31) allows for synthesis of primer-extended cDNA libraries using the DNA polymerase chain reaction technique to amplify copies of the sequence between a single region in the transcript and the 3' or 5' end. The minimum information required for this amplification is a single short stretch of sequence within the mRNA to be cloned. However, since the RACE procedure utilizes the PCR method which can give rise to differential amplification of particular transcripts, no firm conclusions can be reached as to the relative abundance of any newly identified sequence based solely on RACE identification.

RACE cDNA libraries were constructed from adipose tissue, as well as adipose stromal cells that were untreated, or treated with dexamethasone or Bt2cAMP+PDA. By making libraries from cells in culture under the various hormonal conditions, one can then establish if there are new 5' termini and thus determine if alternative promoters are employed in response to changes in the hormonal environment of the cells.

A number of cDNA clones from each library were sequenced in order to estimate the distribution of the alternative 5' sequences. As indicated in Table 1, in addition to the promoter II-specific sequence, four new 5' sequences were identified (FIG. 1). These new sequences are referred to as I.3 and I.4 in the order that they were discovered, and I.3-truncate and I.4 /I.2. All of the new sequences were spliced onto exon II at the same 3'-splice junction as exons I.1 and I.2, upstream of the start of translation, and thus would be expected to encode the same protein. The distribution of the various 5' sequences seemed to be influenced by the hormonal treatment of the cells (Table 1). In adipose tissue, I.4, I.3, and I.3-truncate sequences are present. Three cDNA libraries were made from adipose tissue: two were from breast adipose of two different patients, the other from thigh/calves. No I.4-containing CYP19 transcripts were identified in the library made from thigh/calf tissue, while no I.3 truncate-containing CYP19 transcripts were identified in the libraries made from breast adipose tissue. The difference in distribution of 5' ends in the three adipose tissue libraries could be due to patient to patient variation, or else could be a function of tissue localization. In the stromal cells in culture, the choice of 5'-termini appears to be dependent on the hormonal environment of the cells. Most interestingly, in cells expressing PII-specific sequences, namely cells treated with cAMP+phorbol esters in the absence of serum, no I.4-specific sequences are detected. Conversely, in cells expressing I.4-specific sequences such as dexamethasone-treated cells in the presence of serum, no PII-specific sequences are observed. P450arom transcripts containing exon I.3 are present in adipose tissue as well as in cells in culture under all conditions.

Sequence analysis of the cDNAs revealed that the I.3 and I.3-truncate cDNAs were identical at their 5' ends (FIG. 1). Based on the longest cDNA isolated, the I.3-specific sequence is 205 bp and the I.3-truncate-specific sequence contains 99 bp of the most 5' sequence of exon I.3. The possibility exists that both transcripts are driven by a common promoter. Based on the abundance of I.3 cDNA clones verses I.3-truncate clones, it is likely that P450arom mRNA species containing I.3 sequences are present in higher levels than those containing I.3-truncate sequences. As is the case for the I.3 and I.3-truncate clones, the I.4 and I.4/I.2 clones were found to have overlapping regions. The I.4 /I.2 clone contains exon I.4 sequence at the 5' end followed by 205 bp of exon I.2-specific sequence. This is the first observation of two untranslated exons spliced onto a single P450arom transcript. The presence of I.4 /I.2 clones suggests that exon I.4 is located upstream of exon I.2 in the gene. These 5'-termini are illustrated diagrammatically in FIG. 2.

TABLE 1

Cellular distribution of P450arom 5'-termini identified by the RACE procedure

| Sources of Library | PII | 5'-Sequences Identified by RACE | | | |
|---|---|---|---|---|---|
| | | I.3 | I.4 | I.4/I.2 | I.3-truncate |
| Adipose Tissue: | | | | | |
| Breast - 1 | 0 | 0 | 15 | 0 | 0 |
| Breast - 2 | 0 | 4 | 5 | 0 | 0 |
| Thigh/Calves | 0 | 16 | 0 | 0 | 10 |
| Adipose Stromal Cells in Culture: | | | | | |
| Control - serum | 1 | 3 | 2 | 0 | 1 |
| Dex-treated + Serum | 0 | 4 | 7 | 2 | 2 |
| Bt$_2$cAMP + PDA treated-Serum | 6 | 9 | 0 | 0 | 1 |

Figure 3:
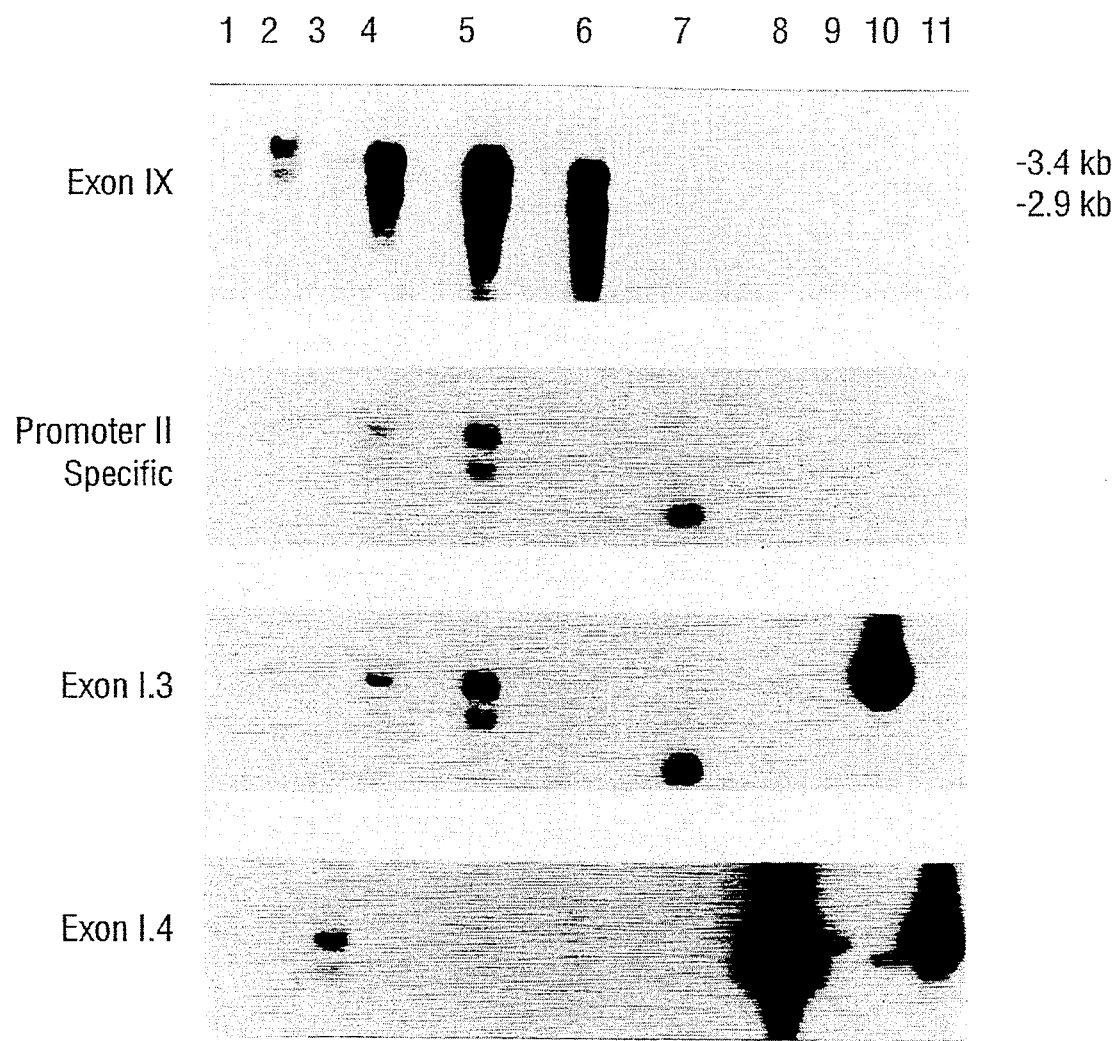
FIG. 3: Northern Analysis of Adipose Tissue and Adipose Stromal Cell poly(A)+RNA. RNA was prepared from a pool of breast and abdominal adpose tissue from several subjects. The relative use of PII-, I.3-, I.4-containing sequences was determined under various hormonal conditions. As indicated on the left, the RNA blot was repeatedly probed using 65-75 bp probes specific to an exon in the coding region (exon IX), as well as PII, I.3, and I.4 sequences. The probes were amplified and labelled by asymmetric PCR. Lane 1—40 µg poly(A)+RNA from whole adipose tissue; lane 2—40 µg poly(A)+RNA from adipose stromal cells in culture+FCS (fetal calf serum); lane 3—20 µg poly(A)+RNA from adipose stromal cells in culture+FCS+250 nM dexamethasone; lane 4—20 µg poly(A)+RNA from adipose stromal cells in culture −FCS+0.5 mM Bt2cAMP; lane 5—20 µg poly(A)+RNA from adipose stromal cells in culture −FCS+0.5 mM Bt2cAMP+100 nM PDA; lane 6—5 µg of placental poly(A)+RNA; lane 7—genomic DNA positive control specific to PII sequences and exon I.3; lane 8—DNA positive control for the exon I.4 probe; lane 9—blank; lane 10—DNA positive control for the exon I.3 probe; lane 11—DNA positive control for the exon I.4 probe.

Northern analysis using exon-specific probes. By means of construction and characterization of cDNA libraries, new 5' sequences were identified and the distribution of these sequences appeared to be influenced by the hormonal treatment of the cells. As mentioned previously characterization of cDNA clones generated by the RACE procedure enables identification of new sequences but may not give an accurate estimate of the relative abundance of transcripts with any particular 5' sequence. In order to obtain better insight into the relative expression of variant 5' ends under different physiological circumstances, northern analysis was performed using sequences specific to the various 5' ends as probes (FIG. 3 and FIG. 4). Poly (A)+RNA from adipose tissue, as well as adipose stromal cells cultured in control medium in the absence of FCS, cells treated with dexamethasone plus FCS, or else with Bt$_2$cAMP or Bt$_2$cAMP+PDA in the absence of FCS, were probed with 65-75 bp fragments specific for each 5' end. The probes were labeled to roughly equal specific activity and equivalent amounts of radioactivity were used in the hybridizations.

Consistent with our findings regarding the RACE libraries, promoter II-specific transcripts were detectable in 20 μg poly(A)+RNA from adipose stromal cells in culture treated with Bt$_2$cAMP or Bt$_2$cAMP+PDA, but not in the same amount of poly(A)+RNA from cells treated with dexamethasone (FIG. 3). The RNA blot in (FIG. 4), which contains 40 82 g poly(A)+RNA per lane was also probed with a PII-specific fragment and again no hybridization was detected in poly(A)+RNA from dexamethasone-treated adipose stromal cells (data not shown). This is the first conclusive evidence of differential expression of 5'-termini under different culture conditions. While a single cDNA clone amplified from control cells maintained in the absence of FCS contained PII-specific sequence, no hybridization to PII-specific probes was detected by northern analysis, suggesting that only a very few P450arom transcripts in untreated cells contain this sequence. As can be seen in (FIG. 3), northern analysis using a probe specific for both I.3 and I.3-truncate sequences revealed hybridization to RNA from control cells maintained in the absence of FCS, from cells treated with Bt$_2$cAMP, or Bt$_2$cAMP+PDA, but not from glucocorticoid-treated This was unexpected since I.3-containing cDNA clones were identified in libraries made from RNA isolated from dexamethasone-treated adipose stromal cells (Table 1). However subsequent northern analysis of 40 μg poly(A)+RNA from dexamethasone-treated adipose stromal cells as well as untreated cells in the absence and presence of FCS, revealed hybridization to an exon I.3-specific probe, although the level of I.4-specific transcripts appeared to be several-fold greater than the level of I.3-specific transcripts (FIG. 4). The fact that the abundance of I.3-containing transcripts in dexamethasone-treated cells is low compared to the abundance of I.4-containing transcripts may explain the lack of I.3-containing transcripts detectable in FIG. 3 where only 20 μg of poly(A)+RNA was used. Alternatively, since the RNA used in the experiment shown in FIG. 3 was prepared from a pool of breast and abdominal adipose tissue from several subjects, whereas that used in FIG. 4 was from breast adipose tissue from two different donors, there may be a region-specific difference in the relative expression of these transcripts. A I.4-specific probe hybridized only to RNA from dexamethasone-treated cells in the presence of FCS (FIG. 3 and FIG. 4). This result is consistent with the absence of P450arom cDNAs containing exon I.4 in libraries from Bt2cAMP- or Bt2cAMP+PDA-treated cells. Additionally, no hybridization of the I.4-specific probe was detected in transcripts from untreated cells either in the absence or presence of FCS (FIG. 4). While dexamethasone-dependent increases in aromatase expression occur only in the presence of FCS, the lack of I.4 transcripts in untreated cells maintained in the presence of FCS suggests that glucocorticoids have a direct action to regulate expression of I.4-containing transcripts, together with growth factor(s) present in the serum. On the other hand, a probe specific for exon I.2 failed to hybridize under any conditions suggesting that I.4/I.2 containing transcripts are present in very low abundance This observation is consistent with the low number of cDNA clones that contain this particular 5' end. These results obtained employing exon-specific northern analysis are summarized in Table 2.

TABLE 2

Summary of major 5'-termini in adipose cells and tissues

| TISSUE/CELLS | Major 5' Terminus |
| --- | --- |
| Adipose Tissue | I.4, I.3 |
| Adipose Stromal Cells in Culture: | |
| Control − Serum | I.3 |
| Control + Serum | I.3 |
| Dex + Serum | I.4, I.3 |
| cAMP − Serum | PII/I.3 |
| cAMP + PDA − Serum | PII/I.3 |
| Ovary | PII |
| Placenta | I.1 |

Figures 5A, 5B:
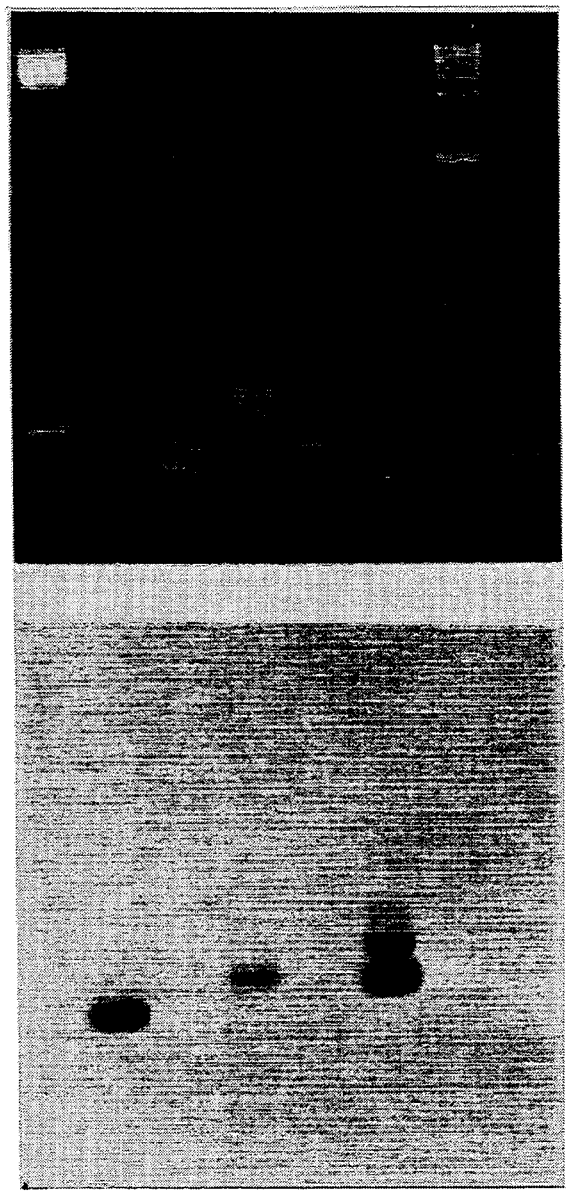
FIG. 5A and FIG. 5B: Reverse Transcriptase—PCR Amplification of Exons I.3 and I.4 from Breast Adipose Tissue. The amplified products were separated on a 2% agarose gel, visualized using ethidium bromide staining (FIG. 5A), transferred to Zetaprobe (BioRad), and probed with an end-labelled oligonucleotide hybridizing to the middle of exon II (FIG. 5B). Lane 1—123 bp molecular weight ladder; lane 2—PCR amplification using exon II-specific primers; lane 3—PCR amplification using exon I.4 -specific primers; lane 4—PR amplification of exon I.4 together with exon II; lane 5—PCR amplification using exon I.3-specific primers; lane 6—PCR amplification of exon I.3 together with exon II; lane 7—1 kb molecular weight ladder; lane 8—no RNA control. The expected sizes of the amplified products were: exon II-183 bp; exon I.4 together with exon II-248 bp; exon I.3 together with exon II-388 bp.

Northern analysis showed that 40 μg of poly (A)+-RNA from adipose tissue failed to hybridize to any CYP19 probe (FIG. 3, lane 1) while a probe specific to the adipose-specific glucose transporter, Glut 4 (34,35), showed readily detectable hybridization (data not shown). Thus although the RNA is intact, CYP19 transcripts in whole adipose tissue are present at levels too low to be detected by northern analysis. As an additional means to verify the presence of exons I.4 and I.3 in adipose tissue, reverse transcriptase-PCR was used to amplify exons I.3 and I.4 separately, and I.3 or I.4 together with exon II (FIG. 5A and FIG. 7B). Total RNA from breast adipose tissue was used as a template for first strand cDNA synthesis. Exon II, the first coding exon, was amplified alone as a positive control. The untranslated exons I.3 and I.4 were amplified together with exon II and so should represent only spliced products. As shown in FIG. 5 (lanes 4 and 6), both exons I.3 and I.4 were readily amplified from adipose tissue in agreement with the observed RACE cDNAs. In lane 6 three bands can be observed. The largest and faintest band at 488 bp represents unspliced RNA products containing exon I.3, a 100 bp intron, and exon II. The second band at 388 bp represents exon I.3 and II together. The smaller band at 282 bp represents the I.3-truncate sequence spliced onto exon II. This experiment is in agreement with the results obtained using the RACE cDNA clones, namely that in whole breast adipose tissue, CYP19 transcripts have alternative 5' ends which include exons I.3 and I.4. However, since both analyses were based on PCR, no conclusions can be made with respect to the relative abundance of these transcripts.

Genomic localization of new CYP19 untranslated exons. At this point it was evident that alternative CYP19-specific 5' termini are expressed in a tissue-specific fashion and that, additionally, these alternative 5' sequences are expressed in adipose stromal cells cultured under different conditions. Since promoter sequences are generally located just 5' of the start site of transcription, expression of these alternative 5' ends may be regulated by alternative promoters. Having identified these new 5' sequences it was then necessary to determine their location in the CYP19 gene, in order to identify the putative promoter sequences regulating expression of these alternative CYP19 transcripts.

Figure 6:
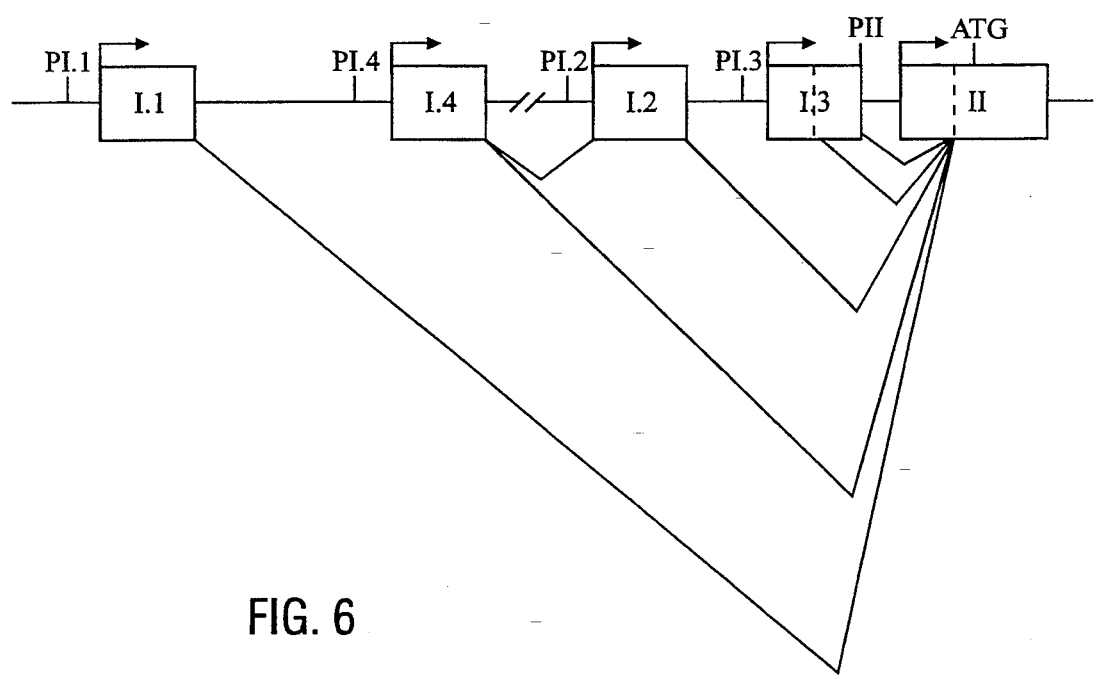
FIG. 6: Structure of the Human CYP19 Gene and Alternative Splicing Patterns Upstream of the Translational Start Site. The four untranslated exons and first coding exon (exon II) are indicated. Promoters I.1 and II and putative promoters I.4, I.2 and I.3 are also indicated. The size of the genomic region shown spans a distance at least 35 kb, but since the genomic clones containing exons I.1 and I.4 on the one hand, and exon I.2 on the other have not been overlapped, the true distance is still unknown.

Upon comparison of exon I.3 to sequences upstream of exon II, exon I.3 was found to be located just upstream of exon II (FIG. 6). A 100 bp intron exists between exons I.3 and II such that promoter II and some of its upstream regulatory sequences are included as exonic sequences in exon I.3-containing P450arom transcripts. Based on the largest cDNA clone isolated containing exon I.3, exon I.3 appears to be approximately 205 bp. It should be noted that a second proximal TATAA sequence exists in the gene 20 bp upstream of the end of the sequence contained in the longest exon I.3-containing clone (27), and 325 bp upstream of the common splice junction in exon II. Furthermore, a sequence, CAAAAT, is present 37 bp upstream of this sequence. Whether or not this region is the promoter sequence regulating expression of I.3-containing transcripts will be determined by primer extension and S1 nuclease protection analysis, as will the exact size of exon I.3.

Figure 7:
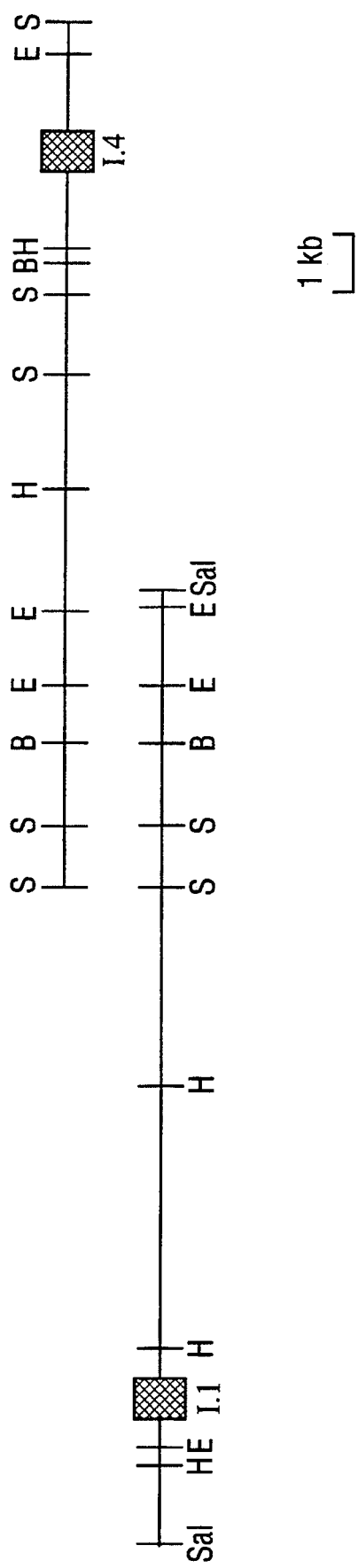
FIG. 7: Restriction Map of Genomic Fragment Containing Exon I.4. The genomic clone is approximately 16 kb, overlaps the genomic fragment containing exon I.1 by 5.7 kb but does not overlap the exon I.2-containing genomic fragment. Exon I.4 is located 20 kb downstream of exon I.1. S-SacI, B-BamHI, E-EcoRI, Sal-SalI.

A comparison of exon I.4 to sequences upstream of exon II revealed no homologies. In addition, Southern analysis of genomic fragments containing exons I.1 or exon I.2 indicated that exon I.4 is not located in these regions of the P450arom gene. Since the genomic clones containing exons I.1 and I.2 did not overlap, a gap remained in the CYP19 gene in the region between exon I.1 and exon I.2. In consideration of the possibility that exon I.4 was located in this region, a human genomic library was screened in hopes of isolating the remainder of the gene. An EMBL-3 SP6/T7 human genomic library was screened using a PCR-labeled 65 bp exon I.4-specific fragment as a probe. A single, 16 kb positive clone was obtained after screening 450,000 pfu (FIG. 7).

The 16 kb insert was cut out of lambda using SacI to release 1.3 kb, 8.5 kb, 1.5 kb, and 4.5 kb fragments. Southern analysis using the exon I.4 probe indicated the presence of exon I.4 in the 4.5 kb Sac I genomic fragment.

In an attempt to determine if the I.4-containing genomic fragment overlapped with genomic clones containing either exons I.1 or I.2, or both, Southern analysis was performed using random-primer labeled fragments corresponding to the 3' end of the exon I.1-containing genomic fragment or the 5' end of the I.2-containing genomic fragment. No hybridization was detected with the I.2-containing fragment, indicative that the I.4 clone did not overlap this region of the gene. However the I.1-containing genomic fragment did hybridize to the I.4-containing genomic clone verifying that these two clones overlapped. Through restriction mapping and Southern analysis, untranslated exon I.4 was estimated to be located 20 kb downstream of exon I.1. The size of the overall gene is therefore estimated to be at least 75 kb. Our current knowledge of the organization of the CYP19 gene upstream from exon II is summarized in FIG. 6, which additionally shows the various splicing possibilities that we have detected.

Characterization of exon I.4. The 4.5 kb SacI fragment containing exon I.4 was subcloned and sequenced (FIG. 8A and FIG. 8B). Upstream from the end of the longest sequence found in the cDNA clones that are no obvious TATA, CAAT or GC-rich sequences which might serve as possible promoter regions. At the same time, the size of I.4 -containing transcripts, as indicated by northern analysis (FIG. 3 and FIG. 4), is such that we would not expect the exonic sequence to extend much further upstream. Primer extension and S1 nuclease protection analysis will have to be undertaken to define the promoter sequences in this region of the gene.

DISCUSSION

Tissue-specific expression of human P450arom. Aromatase is expressed throughout the entire spectrum of the vertebrate phylum. In most species however, expression is confined to the gonads and the brain. In humans and some other higher primates, expression occurs additionally at other sites, in particular, placenta and adipose tissue. Based on the results of this and previous studies, we conclude that in the human, tissue-specific expression of the CYP19 gene is under the control of tissue-specific promoters. The resulting transcripts are generated by means of alternative splicing. Thus, expression in ovary appears to be under the control of a promoter which is proximal to the start of translation (24), similar to the situation in rat (36) and chicken (37). This is likely therefore to be the primordial promoter regulating CYP19 expression. When in the course of evolution the human placenta developed the ability to synthesize estrogens, this promoter was not utilized. Instead, transcripts from placenta contain sequences that are at least 35 kb upstream from the start of translation, apparently under the regulation of a distal promoter I.1 (21). This helps to explain the differences in the regulation of aromatase expression in these two tissues. By contrast, transcripts in adipose contain two different 5'-termini which we have named exon I.3 and exon I.4. Exon I.3 is located just 100 bp upstream of exon II, transcripts containing exon I.3 are formed as a result of a small splicing event and, in fact, contain some of the promoter II region as exonic sequence. Exon I.4 is located 20 kb downstream from exon I.1 and therefore is at least 15 kb upstream from the start of translation. However, since the clone bearing this sequence does not overlap those containing exons I.2 and II, the actual distance is not yet known.

Additionally, a number of other splicing events occur in various tissues giving rise to minor CYP19 transcripts. For example, in placenta, a small percentage of transcripts contain exon I.2, located 9 kb upstream of the start of translation (25). Additionally, in adipose tissue there is a truncated form of I.3 which contains 99 bp of the most 5' sequence of exon I.3, and in adipose stromal cells in culture two clones have been sequenced contain exon I.4 spliced upstream of exon I.2, consistent with the order in which these sequences are located in the gene. However, these all appear to be rare transcripts resulting from infrequent splicing events, as judged by their failure to be visualized by means of exon-specific northern analysis, and their physiological significance, if any, is unclear. Once again, it should be emphasized that all of these untranslated exonic sequences are spliced onto a common 3' splice junction upstream of the start of translation. Consequently, the coding region, and hence the protein product, is identical in each of the tissue sites of expression.

Adipose-specific expression of P450arom. The identification of two previously uncharacterized exonic sequences in the 5' untranslated region of adipose transcripts of CYP19, namely exons I.3 and I.4, defines the nature of CYP19 transcripts in this tissue. Interestingly, the apparently different distribution of I.4 and I.3 transcripts in breast verses thigh/calf adipose tissue gives rise to the possibility of alternative adipose CYP19 transcripts whose expression is dependent on tissue location. Based on the observation of relatively high P450arom expression in lower body fat verses upper body fat, one can speculate that the use of alternative promoters based on tissue location may affect P450arom activity.

It is likely that these newly discovered P450arom transcripts arise due to the use of specific promoters, but these have not been characterized. Upstream of promoter II there is a second TATA-like sequence and CAT-like sequence (21,24,27) which may comprize part of promoter I.3; however, the localization of these elements relative to the transcription start site for exon I.3 has not been determined as yet by means of either primer extension or else S1 nuclease protection analysis. If this is the case then promoter I.3 and promoter II share most of their 5'-regulatory sequences in common. In spite of this, the expression of transcripts with 5'-ends that are specific for each of these promoters in adipose stromal cells in culture is quite different, and dependent upon the hormonal mileau. Similarly, a promoter region responsible for expression of transcripts containing exon I.4 has not yet been identified.

Hormonal regulation of promoter selection in adipose stromal cells in culture. One of the most intriguing aspects of the present study is the observation that the distribution of 5'-termini of CYP19 transcripts in adipose stromal cells in culture is a function of the culture conditions. In particular, promoter II-specific transcripts are present only in cells maintained in the presence of dibutyryl cyclic AMP plus phorbol ester or else dibutyryl cyclic AMP alone, in the absence of FCS. By contrast, transcripts containing exon I.4 are absent under these culture conditions. On the other hand, exon I.4-containing transcripts are present in cells maintained in the presence of dexamethasone plus FCS, whereas promoter II-specific transcripts are entirely absent under these conditions. Exon I.3-specific transcripts on the other hand, appear to be present under all culture conditions including those in which cells are maintained in the absence of stimulatory factors. Based on these findings, we propose that expression of transcripts containing exon I.4 is glucocorticoid-specific, and additionally requires the presence of serum or growth factors. Thus, glucocorticoid stimulation of expression mediated by putative promoter I.4 would lead to the formation of transcripts containing exon I.4 in their 5' termini. By contrast, expression of promoter II-specific sequences appears to be cyclic AMP-mediated. This concept is consistent with the finding that in the ovary, transcripts specific for promoter II are uniquely present (24), whereas those specific for exon I.4 are undetectable. CYP19 expression in human granulosa cells is known to be stimulated by cyclic AMP analogs but not by glucocorticoids. Similarly, a sequence apparently identical to exon I.4 has recently been reported to be present in 5'-termini of CYP19 transcripts in human skin fibroblasts, cells in which aromatase activity is known to be induced by glucocorticoids (38).

An important question which then arises is whether or not enhancement of expression of transcripts from promoters II and I.4 by cyclic AMP and dexamethasone, respectively, is sufficient to determine the splicing pattern required to produce the respective 5'-termini containing promoter II-specific sequence and exon I.4, or whether additional factors are required. Selection of alternative splicing pathways has been found to be an important regulatory step in expression of a number of genes, and regulated splicing can function as an on/off switch in gene expression. The best examples of this to date have been described to occur in Drosophila (39), where several genes controlling sex determination function in a regulatory cascade that operates principally at the level of splicing. Three genes, Sxl, Tra, and Tra2 encode proteins that directly or indirectly modulate splice site selection (40-42). Recently a protein factor, ASF (alternative splicing factor), was isolated from human HeLa cell extracts and shown to alter the selection of alternative 5' splice sites in an SV40 early pre-mRNA when added to in vitro splicing reactions (43-45). An important question which therefore arises regarding hormonal selection of expression of specific CYP19 transcripts is whether the mechanism of alternative splicing is subject to hormonal regulation distinct from and in addition to that governing selection of promoter utilization. Whatever the mechanisms involved, however, to our knowledge this is the first time that in vitro hormonal regulation of alternative promoter usage has been described in a mammalian gene.

Clinical considerations. Althought the physiological role of aromatase activity in human adipose tissue is not clear, it likely has a role to play in the maintenance of bone mineralization and hence prevention of osteoporosis. However, as discussed earlier, the pathophysiological sequelae are more than apparent, namely the implication of estrogen synthesized in adipose in the etiology of both endometrial and breast cancer (46). We have studied the distribution of CYP19 transcripts in breast fat in relation to the localization of a tumor, and have provided evidence that expression is higher in regions proximal to the tumor as compared to distal regions. This is consistent with previous studies in which similar regional variations in aromatase activity were reported (47). These observations lend credence to the view that there is crosstalk between tumor cells and the surrounding adipose cells in terms of control of local production of estrogens, as we have previously suggested (19). We also have recently shown that P450arom expression in adipose tissue displays striking regional as well as age-dependent variations. As indicated in the present study (Table 1), there may be regional variations in promoter usage in different adipose tissue sites, in that transcripts containing exon I.4-specific sequence appear to be present only in breast fat, whereas I.3-specific sequences are present in both upper and lower body fat. It remains to be determined whether alternative promoter usage provides a basis for the age- and region-specific distribution of P450arom expression in human adipose tissue.

ACKNOWLEDGEMENTS

This work was supported, in part, by USPHS grant no. AG08174. Mala S. Mahendroo was supported, in part, by USPHS Training Grant no. 5-T32-HD07190.

REFERENCES

1. Mendelson, C. R., Wright, E. E., Porter, J. C., Evans, C. T. and Simpson, E. R. (1985) *Arch. Biochem. Biophys.* 243, 480-491
2. Nakajin, S., Shimoda, M., and Hall, P. F. (1986) *Biochem. Biophys. Res. Commun.* 134, 704-710
3. Kellis, J. T.,Jr. and Vickery, L. E. (1987)*J. Biol. Chem.* 262, 4413-4420
4. Osawa, Y., Yoshida, N., Franckowiak, M., and Kitawaki, J. (1987) *Steroids* 50, 11-28
5. Nebert, D. W., Nelson, D. R., Adesnik, M., Coon, M. J., Estabrook, R. W., Gonzales, F. J., Guengerich, F. P., Gunsalus, I. C., Johnson, E. F., Kemper, B., Levin, W., Philips, I. R., Sato, R., and Waterman, M. R. (1989) DNA 8, 1-13
6. Thompson, E. A.,Jr. and Siiteri, P. K. (1974) *J. Biol. Chem.* 249, 5373-5378
7. Akhtar, M., Calder, M. R., Corina, D. L., and Wright, J. N. (1982) *Biochem. J.* 201, 569-580
8. Caspi, E., Wicha, J., Arunachalam, T., Nelson, P., and Spiteller, G. (1984) *J. Am. Chem. Soc.* 106, 7282-7283
9. Cole, P. A. and Robinson, C. H. (1988)*J. Am. Chem. Soc.* 110, 1284-1285
10. Goto, J. and Fishman, J. (1977) *Science* 195, 80-81
11. Grodin, J. M., Siiteri, P. K., and MacDonald, P. C. (1973)*J. Clin. Endocrinol. Metab.* 36, 207-214
12. Ryan, K. J. (1959)*J. Biol. Chem.* 134, 268-272
13. Hemsell, D. L., Grodin, J. M., Brenner, P. F., Siiteri, P. K., and MacDonald, P. C. (1974)*J. Clin. Endocrinol. Metab.* 38, 476-479
14. Edman, C. D. and MacDonald, P. C. (1978)*Am. J. Obstet. Gynecol.* 130, 456-461
15. Ackerman, G. E., Smith, M. E., Mendelson, C. R., MacDonald, P. C., and Simpson, E.R. (1981)*J. Clin. Endocrinol. Metab.* 53, 412-417
16. Price, T., Aitken, J., Head, J., Mahendroo, M. S., Means, G. D., and Simpson, E. R. (1992)*J. Clin. Endocrinol. Metab.* 74, 1247-1252
17. Simpson, E. R., Ackerman, G. E., Smith, M. E., and Mendelson, C. R. (1981)*Proc. Natl. Acad. Sci. USA* 78, 5690-5694
18. Mendelson, C. R., Corbin, C. J., Smith, M. E., Smith, J., and Simpson, E. R. (1986) *Endocinology* 118, 968-973
19. Simpson, E. R., Merrill, J. C., Hollub, A. J., Graham-Lorence, S., and Mendelson. C. R. (1989)*Endocr. Rev.* 10, 136-148

20. McAllister, J. M. and Simpson, E. R. (1993)*Endocrinology*, (Submitted)
21. Means, G. D., Mahendroo, M., Corbin. C. J., Mathis, J. M., Powell, F. E., Mendelson, C. R., and Simpson, E. R. (1989)*J. Biol. Chem.* 264, 19385–19391
22. Harada, N., Yamada, K., Saito, K., Kibe, N., Dohmae, S., and Takagi, Y. (1990) *Biochem. Biophys. Res. Commun.* 166, 365–372
23. Toda, K., Terashima, M., Kamamoto, T., Sumimoto, H., Yamamoto, Y., Sagara, Y., Ikeda, H., and Shizuta, Y. (1990)*Eur. J. Blochem.* 193, 559–565
24. Means, G. D., Kilgore, M. W., Mahendroo, M. S., Mendelson, C. R., and Simpson, E. R. (1991) *Mol. Endocrinol.* 5, 2005–2013
25. Kilgore, M. W., Means. G. D., Mendelson, C. R., and Simpson, E. R. (1992)*Mol. Cell. Endocrinol.* 83, R9–R16
26. Toda, K., Miyahara, K., Kawamoto, T., Ikeda, H., Sagara, Y., and Shizuta, Y. (1992) *Eur. J. Blochem.* 205, 303–309
27. Mahendroo, M. S., Means, G. D., Mendelson, C. R., and Simpson, E. R. (1991)*J. Biol. Chem.* 266, 11276–11281
28. Mahendroo, M. S. and Simpson, E. R. (1992)74th *Annual Endocrine Society Meeting* 378(Abstract)
29. Chirgwin, J. M., Przybyla, A. E., MacDonald, R. J., and Rutter, W.J. (1979) *Biochemistry* 18, 5294–5299
30. Frohman, M. A., Dush, M. K., and Martin, G. R. (1988)*Proc. Natl. Acad. Sci. USA* 85, 8998–9002
31. Frohman, M. A. (1990)*Perkin-Elmer Cetus Amplifications*, Perkin-Elmer Cetus, p. 11–14
32. Wood, W. I., Gitschier, J., Lasky, L. A., and Lawn, R. M. (1985)*Proc. Natl. Acad. Sci. USA* 82, 1585–1588
33. Maniatis, T., Fritsch, E. F., and Sambrook, J. (1982)*Molecular Cloning: A laboratory manual*, Cold Spring Harbor Laboratory, Cold Spring Harbor, N.Y.
34. Fukumoto, H., et at. (1989)*J. Biol. Chem.* 264, 7776–7779
35. James, D. E., Stube, M., and Mueckler, M. (1989)*Nature* 338, 83–87
36. Hickey, G. T., Krasnow, J. S., Beattie, W. G., and Richards, J. S. (1990)*Mol. Endocrinol.* 4, 3–12
37. Matsumine, H., Herbst, M. A., Ignatius Ou, S. -H., Wilson, J. D., and McPhaul, M. J. (1991)*J. Biol. Chem.* 266, 19900–19907
38. Harada, N. (1992)*Biochem. Biophys. Res. Commun.* 189, 1001–1007
39. Baker, B. S. (1989)*Nature* 340, 521–524
40. Cline, T. W. (1984)*Genetics* 107.231–277
41. Boggs, R. T., Gregor, P., Idriss, S., Belote, J. M., and McKeown, M. (1987)*Cell* 50, 739–747
42. Nagoshi, R. N., McKeown, M., Butis, K. C., Belote. J. M., and Baker, B. S. (1988) *Cell* 53, 229–236
43. Ge, H. and Manley, J. L. (1990)*Cell* 62, 25–34
44. Krainer, A. R., Mayeda, A., Kozak, D., and Binns, G. (1991)*Cell* 66, 383–394
45. Ge, H., Zuo, P., and Manley, J. L. (1991)*Cell* 66, 373–382
46. Miller, W. R. (1991)*J. Steroid Biochem. Mol. Biol.* 39, 783–790
47. O'Neill, J. S., Elton, R. A., and Miller, W. R. (1988)*Brit. Med. J.* 296, 741–743

---

What is claimed is:

1. A nucleic acid segment comprising a sequence including an I.4 promoter of an aromatase cytochrome P450 gene, the promoter being further defined as directing gene expression in adipose tissue and contained in the nucleotide sequence of SEQ ID NO:7.

* * * * *

UNITED STATES PATENT AND TRADEMARK OFFICE
CERTIFICATE OF CORRECTION

PATENT NO. : 5,446,143

DATED : August 29, 1995

INVENTOR(S) : Evan R. Simpson, Mala S. Mahendro, Carole R. Mendelson

It is certified that error appears in the above-identified patent and that said Letters Patent is hereby corrected as shown below:

Title page, item [57], line 15, delete "gluocorticoids" and insert --glucocorticoids--therefor.

Signed and Sealed this

Fourteenth Day of November, 1995

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 388 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 244..387

( x i ) SEQUENCE DESCRIPTION: SEQ ID NO:1:

```
GGCTTTCAAT  TGGGAATGCA  CGTCACTCTA  CCCACTCAAG  GGCAAGATGA  TAAGGTTCTA         60

TCAGACCAAG  CGTCTAAAGG  AACCTGAGAC  TCTACCAAGG  TCAGAAATGC  TGCAATTCAA        120

GCCAAAAGAT  CTTTCTTGGG  CTTCCTTGTT  TTGACTTGTA  ACCATAAATT  AGTCTTGCCT        180

AAATGTCTGA  TCACATTATA  AAACAGACTC  TAAATTGCCC  CCTCTGAGGT  CAAGGAACAC        240

AAG ATG GTT TTG GAA ATG CTG AAC CCG ATA CAT TAT AAC ATC ACC AGC              288
    Met Val Leu Glu Met Leu Asn Pro Ile His Tyr Asn Ile Thr Ser
    1               5                  10                  15

ATC GTG CCT GAA GCC ATG CCT GCT GCC ACC ATG CCA GTC CTG CTC CTC              336
Ile Val Pro Glu Ala Met Pro Ala Ala Thr Met Pro Val Leu Leu Leu
                20                  25                  30

ACT GGC CTT TTT CTC TTG GTG TGG AAT TAT GAG GGC ACA TCC TCA ATA              384
Thr Gly Leu Phe Leu Leu Val Trp Asn Tyr Glu Gly Thr Ser Ser Ile
```

```
                      35                      40                      45
CCA G                                                                                        3 8 8
Pro
```

( 2 ) INFORMATION FOR SEQ ID NO:2:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Leu Glu Met Leu Asn Pro Ile His Tyr Asn Ile Thr Ser Ile
 1               5                  10                      15

Val Pro Glu Ala Met Pro Ala Ala Thr Met Pro Val Leu Leu Leu Thr
                20                  25                  30

Gly Leu Phe Leu Leu Val Trp Asn Tyr Glu Gly Thr Ser Ser Ile Pro
                35                  40                  45
```

( 2 ) INFORMATION FOR SEQ ID NO:3:

( i ) SEQUENCE CHARACTERISTICS:
        ( A ) LENGTH: 282 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GGCTTTCAAT TGGGAATGCA CGTCACTCTA CCCACTCAAG GGCAAGATGA TAAGGTTCTA    60
TCAGACCAAG CGTCTAAAGG AACCTGAGAC TCTACCAAGG ACTCTAAATT GCCCCTCTG    120
 AGGTCAAGGA ACACAAGATG GTTTGGAAA TGCTGAACCC GATACATTAT AACATCACCA   180
GCATCGTGCC TGAAGCCATG CCTGCTGCCA CCATGCCAGT CCTGCTCCTC ACTGGCCTTT    240
TTCTCTTGGT GTGGAATTAT GAGGGCACAT CCTCAATACC AG                      282
```

( 2 ) INFORMATION FOR SEQ ID NO:4:

( i ) SEQUENCE CHARACTERISTICS:
        ( A ) LENGTH: 505 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
AACCATGACA GCCACAGTCA GGACACAAAA AACAAAGTGT CCTTGATCCC AGGAAACAGC    60
CCTCTGGAAT CTGTGAAATC TAGAAACATA GTTGGGAAAA CTCTGACACC CCTGCCCCAT   120
GACCAACCAA GACTAAGAGT CCCAGAAGAT TGAGGTCACA GAAGGCAGAG GCCTGCCCCC   180
TCTCCAGGAG ATCCCTGACC CATGTGGGGT CATGGGCGGG GCATGAGTGA TGTGATGGGA   240
AACTGGCTCC TGGCTCCAAG TAGAACGTGA CCAACTGGAG CCTGACAGGA GGTCCCTGGC   300
ACTGGTCAGC CCATCAAACC AGGACTCTAA ATTGCCCCCT CTGAGGTCAA GGAACACAAG   360
ATGGTTTTGG AAATGCTGAA CCCGATACAT TATAACATCA CCAGCATCGT GCCTGAAGCC   420
ATGCCTGCTG CCACCATGCC AGTCCTGCTC CTCACTGGCC TTTTCTCTT GGTGTGGAAT   480
TATGAGGGCA CATCCTCAAT ACCAG                                         505
```

( 2 ) INFORMATION FOR SEQ ID NO:5:

( i ) SEQUENCE CHARACTERISTICS:
  ( A ) LENGTH: 439 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:5:

| | | | | | | |
|---|---|---|---|---|---|---|
| AAGTAGAACG | TGACCAACTG | GAGCCTGACA | GGAGGTCCCT | GGCACTGGTC | AGCCCATCAA | 60 |
| ACCAGGACCG | CTGATAACAG | CTTTCATGTG | GAACTTGGGA | TTAATATCAA | GCAAGCCATG | 120 |
| GATTTTGTCT | CCACTGAACT | TGGGCATCAT | GGACAGTTTC | CATTCCAGCA | GTTAAGGGCT | 180 |
| TCCTGACTTT | CAACAGTGGT | GCTGATCCCA | GTTCTGAAGA | GTGGAACATC | AGAGAGCCTC | 240 |
| CCCTCCTCAG | CCACTTGACT | CTAAATTGCC | CCCTCTGAGG | TCAAGGAACA | CAAGATGGTT | 300 |
| TTGGAAATGC | TGAACCCGAT | ACATTATAAC | ATCACCAGCA | TCGTGCCTGA | AGCCATGCCT | 360 |
| GCTGCCACCA | TGCCAGTCCT | GCTCCTCACT | GGCCTTTTC | TCTTGGTGTG | GAATTATGAG | 420 |
| GGCACATCCT | CAATACCAG | | | | | 439 |

( 2 ) INFORMATION FOR SEQ ID NO:6:

( i ) SEQUENCE CHARACTERISTICS:
    ( A ) LENGTH: 262 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| GCACCCTCTG | AAGCAACAGG | AGCTATAGAT | GAACCTTTTA | GGGGATTCTG | TAATTTTCT | 60 |
| GTCCCTTTGA | TTTCCACAGG | ACTCTAAATT | GCCCCCTCTG | AGGTCAAGGA | ACACAAGATG | 120 |
| GTTTTGGAAA | TGCTGAACCC | GATACATTAT | AACATCACCA | GCATCGTGCC | TGAAGCCATG | 180 |
| CCTGCTGCCA | CCATGCCAGT | CCTGCTCCTC | ACTGGCCTTT | TTCTCTTGGT | GTGGAATTAT | 240 |
| GAGGGCACAT | CCTCAATACC | AG | | | | 262 |

( 2 ) INFORMATION FOR SEQ ID NO:7:

( i ) SEQUENCE CHARACTERISTICS:
    ( A ) LENGTH: 1166 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

| | | | | | | |
|---|---|---|---|---|---|---|
| CTCTGGTCAG | ATATTTTGAT | CATGCTACAG | TGCATGAAAT | TGTTCATAAG | AATTGTATGT | 60 |
| GCCTCTGTAT | CTAACAGGAT | CTGCTTATAT | CTTCAGAAAA | CTTTGTCATA | AATTTAAATT | 120 |
| ACTTAAAGTG | TCTGATCTTC | AGATACTTTA | AAGTAGTGCA | TTTGAGAATG | GAATGTTGA | 180 |
| TTACAGTGCG | TATAGGGAAA | TAGATGAATA | TTCCATTAAT | AACTATTAAA | ATCTGCTAAA | 240 |
| GCTTAGGCTA | AGCTGATATA | TTTAGTTGTA | ATAAAATTGG | GTGAACACAT | TCCAACTTCA | 300 |
| GCCTGATTAA | GGGAAAGGGT | GTAGGGGTGA | GACACTTAGG | CGGAGCTTGA | AAAGGAATGG | 360 |
| TGAGAGTTTG | GCCAATGGAA | GGAAGGCTGT | GCCAGACAGG | AATAGTGTGG | GCTGACGACA | 420 |
| ACTGAGGGCA | AAGTGCTTGT | CCCCTCATAG | TTGCGCAATG | AATGCAGAGG | GGCTGAGGTT | 480 |
| CATCTGTCGT | CTTCAGCTCT | GCAGGCTACA | TCTCAGGGTG | TTTCCTGTGA | AAGTTCCAGA | 540 |
| AGAAAGCTGT | ATGGTCAGCT | TGGGGAAATA | TGTGGTTCAT | GCTGGAATGC | TGGACATACC | 600 |

| | | | | | |
|---|---|---|---|---|---|
| ACATTATTGG | AAAGATGCAC | ATTGAATGAC | CGACAAAATG | AAACTCAACT | TTCCAAATGC | 660 |
| TGGTAATGAG | AGAAGATTCT | GTTCTAATGA | CCAGTTGTTT | CCTGAAAGAA | TGTCAGCTCG | 720 |
| ATTCATAATG | AATGCATTCT | AACCATGACA | GCCACAGTCA | GGACACAAAA | AACAAAGTGT | 780 |
| CCTTGATCCC | AGGAAACAGC | CCTCTGGAAT | CTGTGAAATC | TAGAAACATA | GTTGGGAAAA | 840 |
| CTCTGACACC | CCTGCCCAT | GACCAACCAA | GACTAAGAGT | CCCAGAAGAT | TGAGGTCACA | 900 |
| GAAGGCAGAG | GCCTGCCCCC | TCTCCAGGAG | ATCCCTGACC | CATGTGGGGT | CATGGGCGGG | 960 |
| GCATGAGTGA | TGTGATGGGA | AACTGGCTCC | TGGCTCCAAG | TAGAACGTGA | CCAACTGGAG | 1020 |
| CCTGACAGGA | GGTCCCTGGC | ACTGGTCAGC | CCATCAAACC | AGGTAAGTCC | TTGGAGTCTG | 1080 |
| AGTAGGGACA | AGAGACTGTT | CTGTGCTTTG | GCAGGGATCA | GGAAGATGTT | AGAATGTGGT | 1140 |
| TGTTGGAACT | TATCTTTGGA | GCTGAA | | | | 1166 |

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ACTTGCTGAT AATGAGTGTT                    20

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTGGTATTGA GGATATGCCC TCATAAT          27